United States Patent
Li et al.

(10) Patent No.: US 9,402,800 B2
(45) Date of Patent: Aug. 2, 2016

(54) COSMETIC COMPOSITIONS COMPRISING LATEX FILM FORMERS

(71) Applicant: L'OREAL, Paris (FR)

(72) Inventors: Chunhua Li, Scotch Plains, NJ (US); Hy Si Bui, Piscataway, NJ (US); Jean-Thierry Simonnet, Mamroneck, NY (US); Anne Wagner, Philadelphia, PA (US); Ruth Josie Donat, Union, NJ (US)

(73) Assignee: L'OREAL, Paris (FR)

( * ) Notice: Subject to any disclaimer, the term of this patent is extended or adjusted under 35 U.S.C. 154(b) by 43 days.

(21) Appl. No.: 14/348,657

(22) PCT Filed: Oct. 1, 2012

(86) PCT No.: PCT/US2012/058297
§ 371 (c)(1),
(2) Date: Mar. 31, 2014

(87) PCT Pub. No.: WO2013/074210
PCT Pub. Date: May 23, 2013

(65) Prior Publication Data
US 2014/0328780 A1   Nov. 6, 2014

Related U.S. Application Data

(60) Provisional application No. 61/541,173, filed on Sep. 30, 2011.

(51) Int. Cl.
*A61K 8/81* (2006.01)
*A61Q 1/10* (2006.01)
*A61Q 3/02* (2006.01)
*A61K 8/02* (2006.01)

(52) U.S. Cl.
CPC ............ *A61K 8/8152* (2013.01); *A61K 8/0241* (2013.01); *A61K 8/8147* (2013.01); *A61Q 1/10* (2013.01); *A61Q 3/02* (2013.01); *A61K 2800/412* (2013.01); *A61K 2800/594* (2013.01); *A61K 2800/654* (2013.01)

(58) Field of Classification Search
CPC ......... A61Q 1/10; A61Q 3/02; A61K 8/8147; A61K 2800/654; A61K 8/0241; A61K 2800/412; A61K 2800/594; A61K 8/8152
See application file for complete search history.

(56) References Cited

U.S. PATENT DOCUMENTS

| | | | |
|---|---|---|---|
| 3,412,054 A | 11/1968 | Milligan et al. | |
| 6,372,201 B1 | 4/2002 | Leuridan et al. | |
| 6,503,495 B1 | 1/2003 | Alwattari et al. | |
| 6,517,823 B1 | 2/2003 | Norman et al. | |
| 2003/0109630 A1 | 6/2003 | Smith et al. | |
| 2005/0163741 A1* | 7/2005 | Zech | 424/70.16 |
| 2005/0244355 A1 | 11/2005 | Sabino et al. | |
| 2006/0193789 A1 | 8/2006 | Tamarkin et al. | |
| 2007/0224140 A1 | 9/2007 | Quadir et al. | |
| 2009/0068131 A1 | 3/2009 | Malnou | |
| 2009/0136439 A1 | 5/2009 | Feng et al. | |
| 2009/0317432 A1 | 12/2009 | Kergosien | |
| 2010/0021409 A1 | 1/2010 | Alwattari | |
| 2010/0028284 A1 | 2/2010 | Atis et al. | |
| 2010/0080763 A1 | 4/2010 | Kantner et al. | |
| 2011/0020261 A1 | 1/2011 | Bui et al. | |
| 2011/0165102 A1 | 7/2011 | Arditty et al. | |

FOREIGN PATENT DOCUMENTS

| | | |
|---|---|---|
| EP | 2008644 A2 | 12/2008 |
| EP | 2243463 A2 | 10/2010 |
| WO | 2010149493 A2 | 12/2010 |

OTHER PUBLICATIONS

International Search Report and Written Opinion for PCT/US2012/058297.
Written Opinion for PCT/US2012/056806.
Extended European Search Report for co-related EP Application No. 12850523.7 dated Jun. 15, 2015.
English language abstract for EP 2008644A2 (Dec. 31, 2008).
English language abstract for EP 2243463A2 (Oct. 27, 2010).

\* cited by examiner

*Primary Examiner* — Ali Soroush
*Assistant Examiner* — Genevieve S Alley
(74) *Attorney, Agent, or Firm* — The Marbury Law Group, PLLC

(57) ABSTRACT

Disclosed are cosmetic compositions comprising latex film formers chosen from at least one random styrene acrylate copolymer or derivatives thereof, and at least one acrylate copolymer or derivatives thereof, in combination with at least one coalescent and/or plasticizer. Also disclosed are cosmetic compositions comprising at least one latex film forming blend comprising (1) at least one random styrene acrylate copolymer and at least one acrylate copolymer or derivative thereof, or (2) at least two random styrene acrylate copolymers. Polyurethane latex dispersions may be incorporated into the compositions. Optionally, the cosmetic compositions may additionally comprise at least one coalescent and/or plasticizer in combination with the at least one latex film forming blend.

13 Claims, 2 Drawing Sheets

| Raw Material | Raw Material Only | Tributyl Citrate | Texanol Ester Alcohol | Diisobutyl adipate | Propylene Glycol n-Butyl Ether | Dipropylene Glycol Dibenzoate |
|---|---|---|---|---|---|---|
| Syntran KL219 | 20° Shine: 69.1<br>Oil: 5<br>Water: 0<br>Adhesion: 1<br>Hardness: 88 | 20° Shine: 58.3<br>Oil: 5<br>Water: 0<br>Adhesion: 0<br>Hardness: 46 | 20° Shine: 73.0<br>Oil: 5<br>Water: 0<br>Adhesion: 1<br>Hardness: 52 | 20° Shine: 72.5<br>Oil: 5<br>Water: 3<br>Adhesion: 2<br>Hardness: 55 | 20° Shine: 64.5<br>Oil: 5<br>Water: 0<br>Adhesion: 2<br>Hardness: 107 | 20° Shine: 70.8<br>Oil: 5<br>Water: 1<br>Adhesion: 0<br>Hardness: 50 |
| Syntran PC5620 | Poor film | Poor film | 20° Shine: 77.9<br>Oil: 5<br>Water: 5<br>Adhesion: 0<br>Hardness: 104 | 20° Shine: 70.4<br>Oil: 5<br>Water: 1<br>Adhesion: 0<br>Hardness: 68 | Poor film | Poor film |
| Dermacryl AQF | Poor film | 20° Shine: 24.3<br>Oil: NA<br>Water: NA<br>Adhesion: NA<br>Hardness: 59 | 20° Shine: 17.1<br>Oil: NA<br>Water: NA<br>Adhesion: NA<br>Hardness: 72 | 20° Shine: 20.7<br>Oil: NA<br>Water: NA<br>Adhesion: NA<br>Hardness: 75 | Poor film | 20° Shine: 13.0<br>Oil: NA<br>Water: NA<br>Adhesion: NA<br>Hardness: 75 |

FIG. 1A

| Raw Material | Raw Material Only | Tributyl Citrate | Texanol Ester Alcohol | Diisobutyl adipate | Propylene Glycol n-Butyl Ether | Dipropylene Glycol Dibenzoate |
|---|---|---|---|---|---|---|
| Syntran 5760 (paraben free) | Poor film | 20° Shine: 60.5<br>Oil: 5<br>Water: 5<br>Adhesion: 0<br>Hardness: 13 | 20° Shine: 75.4<br>Oil: 5<br>Water: 4<br>Adhesion: 0<br>Hardness: 25 | 20° Shine: 74.7<br>Oil: NA<br>Water: NA<br>Adhesion: NA<br>Hardness: 17 | Poor film | 20° Shine: 77.3<br>Oil: 5<br>Water: 5<br>Adhesion: 0<br>Hardness: 16 |
| Rhoplex P376 | Poor film | 20° Shine: 57.9<br>Oil: 5<br>Water: 5<br>Adhesion: 4<br>Hardness: 11 | 20° Shine: 68.4<br>Oil: 5<br>Water: 5<br>Adhesion: 5<br>Hardness: 16 | 20° Shine: 76.8<br>Oil: NA<br>Water: NA<br>Adhesion:<br>Hardness: 10 | 20° Shine: 67.4<br>Oil: 5<br>Water: 5<br>Adhesion: 4<br>Hardness: 20 | 20° Shine: 74.5<br>Oil: 5<br>Water: 4<br>Adhesion: 4<br>Hardness: 8 |
| Joncryl 77 | 20° Shine: 87.7<br>Oil: 5<br>Water: 2<br>Adhesion: 0<br>Hardness: 55 | 20° Shine: 82.1<br>Oil: 5<br>Water: 5<br>Adhesion: 0<br>Hardness: 39 | 20° Shine: 87.3<br>Oil: 5<br>Water: 0<br>Adhesion: 0<br>Hardness: 22 | 20° Shine: 65.8<br>Oil: 5<br>Water: 0<br>Adhesion: 0<br>Hardness: 21 | Poor film | 20° Shine: 89.7<br>Oil: 5<br>Water: 3<br>Adhesion: 0<br>Hardness: 46 |

FIG. 1B

COSMETIC COMPOSITIONS COMPRISING LATEX FILM FORMERS

CROSS-REFERENCE TO RELATED APPLICATIONS

This is a national stage application of PCT/US2012/058297, filed internationally on Oct. 1, 2012, which claims priority to U.S. Provisional Application No. 61/541,173, filed on Sep. 30, 2011, both of which are incorporated herein by reference in their entireties.

FIELD OF THE DISCLOSURE

The disclosure relates to cosmetic compositions comprising at least one latex film former or at least one latex film forming blend. Latex film formers useful in various embodiments of the disclosure may be chosen from at least one random styrene acrylate copolymer and at least one acrylate copolymer or derivative thereof. Latex film forming blends useful in various embodiments of the disclosure may comprise (1) at least one random styrene acrylate copolymer or derivatives thereof, and at least one acrylate copolymer or derivatives thereof, or (2) at least two random styrene acrylate copolymers or derivatives thereof. In further embodiments, at least one polyurethane latex dispersion may optionally be incorporated into the compositions according to various embodiments of the disclosure. In yet further embodiments, the cosmetic compositions may additionally comprise at least one coalescent and/or plasticizer in combination with the at least one film former. Cosmetic compositions according to various embodiments of the disclosure may have improved properties, such as improved water- and/or oil-resistance, shine, adhesion, hardness, and/or long wear.

BACKGROUND

Film formers are well-known in the cosmetic field. Inclusion of a film former in a cosmetic composition can improve various properties, such as, for example, shine, adhesion, and long wear.

The use of latex film formers in cosmetic compositions is also known, for example, in mascara, hair styling products, topical foundation, sunscreen compositions, and water-based nail enamel. In particular, latex and latex blends have been used to provide extended-wear properties of the cosmetic product into which they are formulated. For example, conventional washable mascara compositions use latex film formers in combination with an oil-in-water emulsion.

There is a desire in the cosmetic industry to provide consumers with products having improved properties such as improved shine, adhesion, and long wear. As such, there is a continuous need to invent novel cosmetic compositions which demonstrate one or more improved property.

It has now been surprisingly discovered that by incorporating latex film formers chosen from at least one random styrene acrylate copolymer or derivatives thereof, and at least one acrylate copolymer or derivatives thereof, in combination with at least one coalescent and/or plasticizer, cosmetic properties such as shine, adhesion, and/or long-wear can be improved. It has also surprisingly been discovered that by combining latex film forming blends comprising either (1) at least one random styrene acrylate copolymer or derivatives thereof, and at least one acrylate copolymer or derivatives thereof, or (2) at least two random styrene acrylate copolymers or derivatives thereof, optionally in combination with at least one coalescent and/or plasticizer, cosmetic properties such as shine, adhesion, and long-wear can be improved. In yet further embodiments, incorporating polyurethane latex dispersions in the compositions may improve properties such as shine, adhesion, and/or long-wear.

DRAWINGS

FIGS. 1A and 1B show data with respect to testing of individual latex film formers and coalescent/plasticizers.

DESCRIPTION OF EXEMPLARY EMBODIMENTS

The disclosure relates, in various embodiments, to cosmetic compositions comprising latex film formers chosen from at least one random styrene acrylate copolymer or derivatives thereof, and at least one acrylate copolymer or derivative thereof, in combination with at least one coalescent and/or plasticizer. In further embodiments, the disclosure relates to cosmetic compositions comprising at least one latex film forming blend, chosen from latex film forming blends comprising (1) at least one random styrene acrylate copolymer or derivatives thereof, and at least one acrylate copolymer or derivatives thereof, and (2) at least two random styrene acrylate copolymers or derivatives thereof. In further embodiments, polyurethane latex dispersions may optionally be incorporated into the compositions. In yet further embodiments, the cosmetic compositions comprising latex film forming blends may optionally comprise at least one coalescent and/or plasticizer in combination with the at least one latex film forming blend.

In various exemplary embodiments, the at least one latex film former or latex film forming blend may be present in the cosmetic composition in a combined amount ranging from about 10% to about 90%, such as about 20% to about 80%, about 25% to about 75%, or about 30% to about 60%. In at least one exemplary embodiment, the at least one latex film former or latex film forming blend is present in the cosmetic composition in a combined amount ranging from about 25% to about 35%, such as about 28% to about 30%.

One embodiment of the disclosure relates to cosmetic compositions comprising at least one latex film forming blend comprising (a) at least one random styrene acrylate copolymer or derivatives thereof, and (b) at least one acrylate copolymer or derivatives thereof. In at least one non-limiting embodiment, the latex film forming blend consists essentially of one random styrene acrylate copolymer and one acrylate copolymer.

Any random styrene acrylate copolymer or derivative thereof may be chosen for the latex film forming blend, and one of skill in the art will, with little or even no routine experimentation, be able to choose an appropriate random styrene acrylate copolymer for the particular application desired. In various embodiments, the at least one random styrene acrylate copolymer may be chosen from those having a glass transition temperature (Tg) ranging from about −15° C. to about 90° C., such as from about 0° C. to about 50° C. By way of example only, a styrene/acrylates/ammonium methacrylate copolymer or a styrene acrylic copolymer may be chosen. Exemplary commercial random styrene acrylate copolymer products that may be used include, but are not limited to, SYNTRAN 5760 (with or without paraben), by Interpolymer Corporation; JONCRYL 77, by BASF Performance Chemicals; and RHOPLEX P376, by Dow Chemical Company.

Any acrylate copolymer or derivative thereof may also be chosen for the latex film forming blend, and one of skill in the art will, with little or even no routine experimentation, be able to choose an appropriate acrylate copolymer for the particular application desired. In various embodiments, the at least one acrylate copolymer or derivative thereof may be chosen from those having a glass transition temperature (Tg) ranging from about 15° C. to about 100° C., such as from about 30° C. to about 70° C. By way of example only, an ammonium acrylates copolymer, an acrylates copolymer, and/or an acrylic polymer or copolymer, and derivatives thereof, may be chosen. Exemplary commercial acrylate copolymer products that may be used include, but are not limited to, DERMACRYL AQF by AkzoNobel; SYNTRAN PC5620 and SYNTRAN KL219, both by Interpolymer Corporation; VINYSOL 1086WP; and ACUDYNE DHR by Dow Chemical Company.

A further embodiment of the disclosure relates to cosmetic compositions comprising at least one latex film forming blend comprising at least two random styrene acrylate copolymers. In at least one non-limiting embodiment, the latex film forming blend consists essentially of two random styrene acrylate copolymers.

Any random styrene acrylate copolymer or derivative thereof may be chosen for the latex film forming blend, and one of skill in the art will, with little or even no routine experimentation, be able to choose appropriate random styrene acrylate copolymers for the particular application desired. In various embodiments, each of the at least two random styrene acrylate copolymers may be chosen from those having a glass transition temperature (Tg) ranging from about −15° C. to about 90° C., such as from about 0° C. to about 50° C. By way of example only, a styrene/acrylates/ammonium methacrylate copolymer or a styrene acrylic copolymer may be chosen. Exemplary commercial random styrene acrylate copolymer products that may be used include, but are not limited to, SYNTRAN 5760 (with or without paraben), by Interpolymer Corporation; JONCRYL 77, by BASF Performance Chemicals; and RHOPLEX P376, by Dow Chemical Company.

Yet a further embodiment of the disclosure optionally incorporates at least one polyurethane latex dispersion into the compositions according to various exemplary embodiments. By way of non-limiting example, suitable latexes include aqueous polyurethane dispersions including the reaction products of:

A) a prepolymer according to the formula:

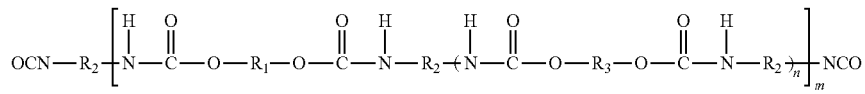

wherein R1 represents a bivalent radical of a dihydroxyl functional compound, R2 represents a hydrocarbon radical of an aliphatic or cycloaliphatic polyisocyanate, R3 represents a radical of a low molecular weight diol, optionally substituted with ionic groups, n is from 0 to 5, and m is >1;

B) at least one chain extender according to the formula: H2N—R4-NH2 wherein R4 represents an alkylene or alkylene oxide radical not substituted with ionic or potentially ionic groups; and C) at least one chain extender according to the formula: H2N—R5-NH2 wherein R5 represents an alkylene radical substituted with ionic or potentially ionic groups.

Suitable dihydroxyl compounds for providing the bivalent radical R1 include those having two hydroxy groups and having number average molecular weights of from about 700 to about 16,000, and preferably from about 750 to about 5000.

Examples of the high molecular weight compounds include polyester polyols, polyether polyols, polyhydroxy polycarbonates, polyhydroxy polyacetals, polyhydroxy polyacrylates, polyhydroxy polyester amides, polyhydroxy polyalkadienes and polyhydroxy polythioethers. The polyester polyols, polyether polyols and polyhydroxy polycarbonates may be chosen in at least certain exemplary embodiments. Mixtures of various such compounds are also within the scope of the disclosure.

Suitable polyisocyanates for providing the hydrocarbon radical R2 include organic diisocyanates having a molecular weight of from about 112 to about 1,000, such as from about 140 to about 400. Optional diisocyanates are those represented by the general formula R2(NCO)2 indicated above, in which R2 represents a divalent aliphatic hydrocarbon group having from 4 to 18 carbon atoms, a divalent cycloaliphatic hydrocarbon group having from 5 to 15 carbon atoms, a divalent araliphatic hydrocarbon group having from 7 to 15 carbon atoms or a divalent aromatic hydrocarbon group having from 6 to 15 carbon atoms. Examples of the organic diisocyanates which are suitable include tetramethylene diisocyanate, 1,6-hexamethylene diisocyanate, dodecamethylene diisocyanate, cyclohexane-1,3- and -1,4-diisocyanate, 1-isocyanato-3-isocyanatomethyl-3,5,5-trimethylcyclohexane (isophorone diisocyanate or IPDI), bis-(4-isocyanatocyclohexyl)-methane, 1,3- and 1,4-bis(isocyanatomethyl)-cyclohexane, bis-(4-isocyanato-3-methyl-cyclohexyl)-methane, isomers of toluene diisocyanate (TDI) such as 2,4-diisocyanatotoluene, 2,6-diisocyanatotoluene, mixtures of these isomers, hydrogenated TDI, 4,4'-diisocyanato diphenyl methane and its isomeric mixtures with 2,4'- and optionally 2,2'-diisocyanato diphenylmethane, and 1,5-diisocyanatonaphthalene. Mixtures of diisocyanates can, of course, be used in various embodiments. Optional diisocyanates are chosen for aliphatic and cycloaliphatic diisocyanates, such as, for example, 1,6-hexamethylene diisocyanate and isophorone diisocyanate.

"Low molecular weight dials" in the context of R3 means diols having a molecular weight from about 62 to about 700, preferably about 62 to about 200. They may contain aliphatic, alicyclic or aromatic groups. In certain exemplary embodiments, the compounds contain only aliphatic groups. The low molecular weight diols having up to about 20 carbon atoms per molecule include ethylene glycol, diethylene glycol, propane 1,2-dial, propane 1,3-diol, butane 1,4-dial, butylene 1,3-glycol, neopentyl glycol, butyl ethyl propane diol, cyclohexane diol, 1,4-cyclohexane dimethanol, hexane 1,6-diol, bisphenol A (2,2-bis(4-hydroxyphenyl)propane), hydrogenated bisphenol A (2,2-bis(4-hydroxycyclohexyl)propane), and mixtures thereof. Optionally, the low molecular weight diols may contain ionic or potentially ionic groups. Suitable lower molecular weight dials containing ionic or potentially ionic groups are those disclosed in U.S. Pat. No. 3,412,054, the contents of which is hereby incorporated by reference. Preferred compounds include dimethylol butanoic acid (DMBA), dimethylol propionic acid (DMBA) and carboxyl-containing caprolactone polyester dial. If lower molecular weight dials containing ionic or potentially ionic groups are used, they may optionally be used in an amount such that <0.30 meq of COOH per gram of polyurethane in the polyurethane dispersion are present.

The prepolymer is a chain extended using two classes of chain extenders. First, compounds having the formula: H2N—R4-NH2, wherein R4 represents an alkylene or alkylene oxide radical not substituted with ionic or potentially ionic groups. Alkylene diamines include hydrazine, ethylenediamine, propylenediamine, 1,4-butylenediamine and piperazine. The alkylene oxide diamines include 3-{2-[2-(3-aminopropoxy)ethoxy]ethoxy}propylamine (also known as dipropylamine diethyleneglycol or DPA-DEG available from Tomah Products, Milton, Wis.), 2-methyl-1,5-pentanediamine (Dytec A from DuPont), hexane diamine, isophorone diamine, and 4,4-methylenedi-(cyclohexylamine), and the DPA-series ether amines available from Tomah Products, Milton, Wis., including dipropylamine propyleneglycol, dipropylamine dipropyleneglycol, dipropylamine tripropyleneglycol, dipropylamine poly(propylene glycol), dipropylamine ethyleneglycol, dipropylamine poly(ethylene glycol), dipropylamine 1,3-propane diol, dipropylamine 2-methyl-1,3-propane diol, dipropylamine 1,4-butane diol, dipropylamine 1,3-butane diol, dipropylamine 1,6-hexane diol and dipropylamine cyclohexane-1,4-dimethanol. Mixtures of the listed diamines may also be used.

The second class of chain extenders are compounds having the formula: H2N—R5-NH2 wherein R5 represents an alkylene radical substituted with ionic or potentially ionic groups. Such compounds have an ionic or potentially ionic group and two groups that are reactive with isocyanate groups. Such compounds contain two isocyanate-reactive groups and an ionic group or group capable of forming an ionic group. The ionic group or potentially ionic group can be chosen from ternary or quaternary ammonium groups, groups convertible into such groups, carboxyl groups, carboxylate groups, sulfonic acid groups, and sulfonate groups. The at least partial conversion of the groups convertible into salt groups of the type mentioned may take place before or during the mixing with water. Specific compounds include diaminosulfonates, such as for example the sodium salt of N-(2-aminoethyl)-2-aminoethane sulfonic acid (AAS) or the sodium salt of N-(2-aminoethyl)-2-aminopropionic acid.

Commercially available examples of such latexes include, but are not limited to, aqueous polyurethane dispersions comprising a reaction product of a prepolymer comprising a dihydroxyl compound, a polyisocyanate, and a low molecular weight diol and at least two diamine compounds and wherein the composition is substantially free of triethanolamine stearate such as, for example, those sold under the BAYCUSAN® name by Bayer such as, for example, BAYCUSAN® C1000 (polyurethane-34), BAYCUSAN® C1001 (polyurethane-34), BAYCUSAN® C1003 (polyurethane-32), and BAYCUSAN® C1004 (polyurethane-35).

Other examples of polyurethane dispersions can also be used. Examples include Polyurethane 4, 11, 14, 15, 18, 19, 25, 26, 32, 33, 34, 35, 48, etc. Among these, the BAYCUSAN® name by Bayer such as, for example, BAYCUSAN® C1000 (polyurethane-34), BAYCUSAN® C1001 (polyurethane-34), BAYCUSAN® C1003 (polyurethane-32), and BAYCUSAN® C1004 (polyurethane-35) may be chosen. And BAYCUSAN® C1001 (polyurethane-34) is particularly useful according to at least certain exemplary embodiments.

In various exemplary embodiments according to the disclosure, the cosmetic compositions comprising at least one latex film forming blend may optionally further comprise at least one coalescent and/or plasticizer. It is known that inclusion of a coalescent agent promotes the coalescence of polymer particles in an aqueous dispersion, and inclusion of a plasticizer makes it possible to plasticize a polymer in an aqueous dispersion. Any coalescent and/or plasticizer may be used, and one of skill in the art will be able to choose an appropriate coalescent and/or plasticizer with little or no routine experimentation based on, for example, the type of cosmetic composition being formulated and the desired properties thereof.

When included in cosmetic compositions comprising at least one latex film forming blend as described herein, the coalescent and/or plasticizer may be added in a combined amount of up to about 10%, such as up to about 7%, or up to about 5%. In various exemplary embodiments, the coalescent and/or plasticizer may be added in a combined amount ranging from about 1% to about 5%, such as about 1% to about 3%.

Optional coalescents and/or plasticizers useful according to various exemplary embodiments of the disclosure include, but are not limited to, those disclosed in U.S. Pat. No. 6,372,201. By way of example only, optional plasticizers may be chosen from tributyl citrate, texanol ester alcohol, diisobutyl adipate, the ester of tertbutyl acid and 2,2,4-trimethylpentane-1,3-diol, diethyl adipate, diethyl phthalate, dibutyl phthalate, dioctyl phthalate, butyl 2-ethylhexyl phthalate, dimethyl sebacate, dibutyl sebacate, ethyl stearate, 2-ethylhexyl palmitate, dipropylene glycol n-butyl ether, and mixtures thereof. By way of example only, optional coalescents may be chosen from propylene glycol n-butyl ether, dipropylene glycol dibenzoate, dipropylene glycol dimethyl ether, propylene glycol methyl ether acetate, propylene glycol propyl ether, methyl lactate, ethyl lactate, isopropyl lactate, and mixtures thereof.

Yet a further embodiment of the disclosure relates to cosmetic compositions comprising at least one latex film former chosen from (a) at least one random styrene acrylate copolymer or derivatives thereof, and (b) at least one acrylate copolymer or derivatives thereof, in combination with a coalescent and/or plasticizer. Any random styrene acrylate copolymer or derivative thereof, at least one acrylate copolymer or derivative thereof, and coalescent and/or plasticizer as described herein above, may be used.

In addition, other cosmetic ingredients may be included in the compositions according to the disclosure. Such ingredients are known, and include but are not limited to solvents (including water), colorants, humectants, emulsifiers, surfactants, preservatives, fragrances, thickeners or texturizers, emollients, and additional film-formers and coalescents/plasticizers. One of skill in the art will be able to select appropriate types and amounts of additional cosmetic ingredients, based on, for example, the type of cosmetic composition being formulated and the desired properties thereof. By way of example only, such additional cosmetic ingredients may be present in the compositions according to the disclosure in a combined amount ranging from about 10% to about 80%, such as about 15% to about 60%, about 25% to about 40%, or about 30% to about 35%.

Exemplary cosmetic compositions contemplated according to the disclosure include compositions intended for application to keratinous fibers, such as the hair, skin, and nails. Such compositions include, but are not limited to, nail compositions (e.g. nail enamel), mascara compositions, make-up compositions (e.g. foundations), sunscreen compositions, and hair-care compositions (e.g. hair-styling compositions).

Without wishing to be bound by theory, it is believed that the combination of at least one latex film former, e.g. chosen from (a) at least one random styrene acrylate copolymer or derivatives thereof, and (b) at least one acrylate copolymer or derivatives thereof, in combination with a coalescent and/or plasticizer, as well as at least one latex film forming blend comprising (1) at least one random styrene acrylate copolymer and at least one acrylate copolymer or derivative thereof, or (2) at least two random styrene acrylate copolymers, surprisingly and unexpectedly shows a synergistic effect, imparting improved properties such as, for example, improved water- and/or oil-resistance, shine, adhesion, hardness, and/or long-wear to the cosmetic compositions. By way of example only, mascara formulations comprising a latex film forming blend comprising (1) at least one random styrene acrylate copolymer and at least one acrylate copolymer or derivative thereof, or (2) at least two random styrene acrylate copolymers, have been found to have improved curl, curl-retention, volume, and long-wear properties, which are seen for several days after application. As a further non-limiting example, nail formulations, such as water-based nail enamel formulations, comprising a latex film forming blend comprising (1) at least one random styrene acrylate copolymer and at least one acrylate copolymer or derivative thereof, or (2) at least two random styrene acrylate copolymers, have been found to have improved shine, smoothness on application, hardness, and long-wear properties. It should be noted, however, that compositions according to the disclosure may not have one or more of the above-referenced improved properties, yet such compositions are intended to be within the scope of the disclosure.

It is to be understood that both the foregoing description and the following Examples are exemplary and explanatory only, and are not to be interpreted as restrictive of the disclosure. Moreover, it should be understood that various features and/or characteristics of differing embodiments herein may be combined with one another. It is therefore to be understood that numerous modifications may be made to the illustrative embodiments and that other arrangements may be devised without departing from the scope of the invention. Other embodiments will be apparent to those skilled in the art from consideration of the disclosure and practice of the various exemplary embodiments disclosed herein.

It is also to be understood that, as used herein the terms "the," "a," or "an," mean "at least one," and should not be limited to "only one" unless explicitly indicated to the contrary. Thus, for example, the use of "a plasticizer" is intended to mean at least one plasticizer.

Unless otherwise indicated, all numbers used in the specification and claims are to be understood as being modified in all instances by the term "about," whether or not so stated. It should also be understood that the precise numerical values used in the specification and claims form additional embodiments of the invention, and are intended to include any ranges which can be narrowed to any two end points disclosed within the exemplary ranges and values provided. Efforts have been made to ensure the accuracy of the numerical values disclosed herein. Any measured numerical value, however, can inherently contain certain errors resulting from the standard deviation found in its respective measuring technique.

EXAMPLES

The following Examples are intended to be non-restrictive and explanatory only, with the scope of the invention being defined by the claims.

Examples 1 and 2

Simple Mascara Compositions

Two simple mascara compositions were made by mixing, independently, the components set forth in the following Table 1 and Table 2.

TABLE 1

| Trade Name | INCI Name | Weight % |
|---|---|---|
| DERMACRYL AQF | ammonium acrylates copolymer | 43.75 |
| JONCRYL77 | styrene/acrylates copolymer | 43.75 |
| SCANDINOL SP 21 | Tributyl Citrate | 2.2 |
| Distinctive Ink Black PV AQII | Black 2 | 5 |
| Expert Gel EG56 | Bis-Methoxy PEG-13 PEG-438/ PPG-110 SMDI Copolymer | 1 |
| QS Water | QS Water | 4.3 |
| TOTAL | | 100% |

TABLE 2

| Trade Name | INCI Name | Weight % |
|---|---|---|
| DERMACRYL AQF | ammonium acrylates copolymer | 43.75 |
| JONCRYL77 | styrene/acrylates copolymer | 43.75 |
| SCANDINOL SP 21 | Tributyl Citrate | 1.5 |
| | Dipropylene Glycol Dibenzoate | 1.5 |
| QS Water | QS Water | 9.5 |
| TOTAL | | 100% |

Examples 3 and 4

Mascara Compositions

Three mascara compositions were prepared having the compositions shown in Table 3 (one batch) and Table 4 (two batches), independently by following the procedure set forth in Table 5.

TABLE 3

| Phase | INCI Name | Trade Name | Conc. | Weight (g) |
|---|---|---|---|---|
| A1 | DI Water | DI Water | 29.43 | 294.30 |
| A1 | Methylparaben | Methyl Paraben | 0.33 | 3.30 |
| A1 | Phenoxyethanol | Phenoxyethanol | 0.84 | 8.40 |
| A1 | Ethylparaben | Ethyl Paraben | 0.22 | 2.20 |
| A1 | Disodium EDTA | Disodium EDTA | 0.20 | 2.00 |
| A1 | Sodium Dehydroacetate | Sodium Dehydroacetate | 0.20 | 2.00 |
| A1 | Butylene Glycol | Butylene Glycol | 2.40 | 24.00 |
| A1 | Simethicone | Simethicone | 0.10 | 1.00 |
| A1 | PEG-200 Glyceryl Stearate | SIMULSOL 220 | 3.00 | 30.00 |
| A2 | Black Iron Oxide | Sunpuro Black | 7.000 | 70.00 |
| A3 | ACRYLAMIDE/SODIUM ACRYLOYLDIMETHYLTAURATE COPOLYMER | SIMULGEL 600 | 2.00 | 20.00 |

TABLE 3-continued

| Phase | INCI Name | Trade Name | Conc. | Weight (g) |
|---|---|---|---|---|
| B1 | Beeswax | White Beeswax SP 453P | 7.18 | 71.80 |
| B1 | Carnauba Wax | Carnauba Wax SP63 | 4.00 | 40.00 |
| B1 | Cetyl Alcohol | Acilol 16 | 2.00 | 20.00 |
| B1 | VP/EICOSENE COPOLYMER | Antaton V220 | 2.00 | 20.00 |
| B1 | Glyceryl Stearate | Glyceryl Stearate | 1.00 | 10.00 |
| B1 | ETHYLENEDIAMINE/STEARYL DIMER DILINOLEATE COPOLYMER | UNICLEAR 100VG | 2.00 | 20.00 |
| B1 | *SIMMONDSIA CHINENSIS* (JOJOBA) BUTTER | ISO JOJOBA 50 | 2.00 | 20.00 |
| C | AMMONIUM METHACRYLATE COPOLYMER | SYNTRAN 5760 | 25.00 | 250.00 |
| C | ACRYLATES COPOLYMER | SYNTRAN 5100 | 5.00 | 50.00 |
| D | Caprylyl Glycol | Caprylyl Glycol | 1.00 | 10.00 |
| D | Denatured Alcohol | Denatured Alcohol | 3.00 | 30.00 |
| D | Soluble Collagen | Soluble Collagen | 0.10 | 1.00 |
| TOTAL | | | 100.00 | 1000.00 |

TABLE 4

| Phase | INCI Name | Trade Name | Conc. | Weight (g) | Weight (g) |
|---|---|---|---|---|---|
| A1 | DI Water | DI Water | 29.43 | 294.30 | 147.15 |
| A1 | Methylparaben | Methyl Paraben | 0.33 | 3.30 | 1.65 |
| A1 | Phenoxyethanol | Phenoxyethanol | 0.84 | 8.40 | 4.20 |
| A1 | Ethylparaben | Ethyl Paraben | 0.22 | 2.20 | 1.10 |
| A1 | Disodium EDTA | Disodium EDTA | 0.20 | 2.00 | 1.00 |
| A1 | Sodium Dehydroacetate | Sodium Dehydroacetate | 0.20 | 2.00 | 1.00 |
| A1 | Butylene Glycol | Butylene Glycol | 2.40 | 24.00 | 12.00 |
| A1 | Simethicone | Simethicone | 0.10 | 1.00 | 0.50 |
| A1 | PEG-200 Glyceryl Stearate | SIMULSOL 220 | 3.00 | 30.00 | 15.00 |
| A2 | Black Iron Oxide | Sunpuro Black | 7.000 | 70.00 | 35.00 |
| A3 | ACRYLAMIDE/SODIUM ACRYLOYLDIMETHYLTAURATE COPOLYMER | SIMULGEL 600 | 2.00 | 20.00 | 10.00 |
| B1 | Beeswax | White Beeswax SP 453P | 7.18 | 71.80 | 35.90 |
| B1 | Carnauba Wax | Carnauba Wax SP63 | 4.00 | 40.00 | 20.00 |
| B1 | Cetyl Alcohol | Acilol 16 | 2.00 | 20.00 | 10.00 |
| B1 | VP/EICOSENE COPOLYMER | Antaton V220 | 2.00 | 20.00 | 10.00 |
| B1 | Glyceryl Stearate | Glyceryl Stearate | 1.00 | 10.00 | 5.00 |
| B1 | ETHYLENEDIAMINE/STEARYL DIMER DILINOLEATE COPOLYMER | UNICLEAR 100VG | 2.00 | 20.00 | 10.00 |
| B1 | *SIMMONDSIA CHINENSIS* (JOJOBA) BUTTER | ISO JOJOBA 50 | 2.00 | 20.00 | 10.00 |
| C | Joncryl 77/Dermacryl AQF/ 1.5% Tributyl Citrate | | 30.00 | 300.00 | 150.00 |
| D | Caprylyl Glycol | Caprylyl Glycol | 1.00 | 10.00 | 5.00 |
| D | Denatured Alcohol | Denatured Alcohol | 3.00 | 30.00 | 15.00 |
| D | Soluble Collagen | Soluble Collagen | 0.10 | 1.00 | 0.50 |
| TOTAL | | | 100.00 | 1000.00 | 500.00 |

TABLE 5

| Operation | Scraper RPM | Agitator RPM | Homo RPM | VAC Bar | TEMP ° C. |
|---|---|---|---|---|---|
| Charge Phase A1 and Phase A2 to Main Kettle (MK) and mix for 60 minutes to properly disperse pigments. Begin heating to 55° C. | 0 | 0 | 800 | — | RT/55 |
| Charge Phase A3 to MK and mix for 5 minutes. Batch will become thicker as A3 becomes incorporated. Continue heating to 95° C. | 0 | 0 | 1100 | — | 55/95 |
| Melt Phase B1 in Side Kettle (SK) on Hot Plate. | | | Hot Plate | | |
| Heat to 95° C. and verify all waxes are melted. Charge SK to MK and emulsify for 20 minutes. Maintain temperature at 95° C. | 0 | 0 | 1500 | — | 95 |
| Start cooling batch to 45° C. with sweep mixing only. | Min | — | — | — | 95/45 |
| At 45° C., add Phase C one component at a time. Mix until dispersed and uniform. Increase mixer speed if needed to properly | Min | — | — | — | 45 |

TABLE 5-continued

| Operation | Scraper RPM | Agitator RPM | Homo RPM | VAC Bar | TEMP ° C. |
|---|---|---|---|---|---|
| incorporate large amount of film formers added at this stage. | | | | | |
| Continue cooling to 30° C. with sweep mixing. | Min | — | — | — | 45/30 |
| At 30° C., charge Phase D to MK and mix until uniform. | Min | — | — | — | 30 |

The mascara formulations prepared in Tables 1 and 4 above were tested on eyelashes. The resulting products demonstrated improved properties of thickness, curl, volume, and long wear. These properties were still visible after two days.

Example 5

Water-Based Nail Enamel

A water-based nail enamel was prepared having the following composition, as shown in Table 6:

TABLE 6

| INCI Name | Trade Name | Weight % (Raw Material) | Weight % (Active) |
|---|---|---|---|
| Water | Water | 8.11 | qs |
| Styrene acrylic emulsion | RHOPLEX P376 | 20 | 10 |
| Acrylic copolymer | DERMACRYL AQF | 55.55 | 25 |
| Propylene glycol n-butyl ether | DOWANOL PNB | 2.1 | 2 |
| Dipropylene glycol dibenzoate | | 2 | 2 |
| Pigment dispersion | | 12.24 | 3 |
| TOTAL | | 100 | 100 |

The nail enamel composition was tested and found to have improved properties of shine, smoothness upon application, water- and oil-resistance, hardness, and long wear. These properties were seen to last for several days.

What is claimed is:

1. A cosmetic composition comprising at least one latex film forming blend comprising:
   a. at least one random styrene acrylate copolymer having a Tg ranging from about 0° C. to about 50° C.; and
   b. at least one acrylate copolymer or derivative thereof having a Tg ranging from about 30° C. to about 70° C.

2. The cosmetic composition of claim 1, wherein the at least one random styrene acrylate copolymer is chosen from styrene/acrylates/ammonium methacrylate copolymers and styrene acrylic copolymers.

3. The cosmetic composition of claim 1, wherein the at least one acrylate copolymer or derivative thereof is chosen from ammonium acrylates copolymers, acrylates copolymers, acrylic copolymers, and derivatives thereof.

4. The cosmetic composition of claim 1, wherein the latex film forming blend is present in the cosmetic composition in a combined amount ranging from about 20% to about 80%.

5. The cosmetic composition of claim 1, further comprising a coalescent and/or plasticizer.

6. The cosmetic composition of claim 5, wherein the at least one coalescent is chosen from propylene glycol n-butyl ether and dipropylene glycol benzoate, and/or the at least one plasticizer is chosen from tributyl citrate, texanol ester alcohol, and diisobutyl adipate.

7. The cosmetic composition of claim 1, chosen from nail compositions, make-up compositions, mascara compositions, hair-care compositions, and sunscreen compositions.

8. The cosmetic composition of claim 1, further comprising at least one polyurethane latex dispersion.

9. A method of improving at least one property chosen from adhesion, water-resistance, oil-resistance, shine, and long-wear properties in a cosmetic composition, said method comprising including in the cosmetic composition a latex film forming blend chosen from latex film forming blends comprising:
   (1) at least one random styrene acrylate copolymer having a Tg ranging from about 0° C. to about 50° C. and at least one acrylate copolymer or derivative thereof having a Tg ranging from about 30° C. to about 70° C.

10. The method of claim 9, said method further comprising adding at least one coalescent and/or plasticizer to said cosmetic composition.

11. The method of claim 10, wherein the at least one coaslescent is chosen from propylene glycol n-butyl ether and dipropylene glycol benzoate, and/or the at least one plasticizer is chosen from tributyl citrate, texanol ester alcohol, and diisobutyl adipate.

12. The method of claim 9, wherein the cosmetic composition is chosen from nail compositions, make-up compositions, hair-care compositions, and sunscreen compositions.

13. The method of claim 9, further comprising including at least one polyurethane latex dispersion in the cosmetic composition.

* * * * *